US012806541B2

(12) United States Patent
Kamat et al.

(10) Patent No.: US 12,806,541 B2
(45) Date of Patent: Nov. 24, 2026

(54) FALLING FILM APPARATUS AND METHOD FOR USING

(71) Applicant: Dow Global Technologies LLC, Midland, MI (US)

(72) Inventors: Pritish M. Kamat, Houston, TX (US); Paul A. Gillis, Lake Jackson, TX (US); Mohan V. Punganur, Richwood, TX (US); Fermin Alejandro Sandoval, Pearland, TX (US); Robert Norman Jones, Freeport, TX (US); Joseph B. Elliott, Cypress, TX (US); Thomas J. Parsons, Midland, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 111 days.

(21) Appl. No.: 18/685,572

(22) PCT Filed: Aug. 30, 2022

(86) PCT No.: PCT/US2022/042001
§ 371 (c)(1),
(2) Date: Feb. 22, 2024

(87) PCT Pub. No.: WO2023/043609
PCT Pub. Date: Mar. 23, 2023

(65) Prior Publication Data

US 2025/0128182 A1 Apr. 24, 2025

Related U.S. Application Data

(60) Provisional application No. 63/245,906, filed on Sep. 19, 2021.

(51) Int. Cl.
*B01D 1/06* (2006.01)
*C07C 263/20* (2006.01)

(52) U.S. Cl.
CPC ............ *B01D 1/065* (2013.01); *C07C 263/20* (2013.01)

(58) Field of Classification Search
CPC ....... B01D 1/06–065; B01D 53/18–185; B01J 10/02
See application file for complete search history.

(56) References Cited

U.S. PATENT DOCUMENTS

| | | | |
|---|---|---|---|
| 3,370,635 | A | 2/1968 | Kuman |
| 3,849,232 | A | 11/1974 | Kessler |
| 4,154,642 | A | 5/1979 | Mattern |
| 4,199,537 | A | 4/1980 | Zardi |

(Continued)

FOREIGN PATENT DOCUMENTS

| | | | |
|---|---|---|---|
| JP | H07285925 | A | 10/1995 |
| JP | 2002062080 | A | 2/2002 |

(Continued)

*Primary Examiner* — Renee Robinson
(74) *Attorney, Agent, or Firm* — Warner Norcross + Judd LLP

(57) ABSTRACT

A falling film apparatus has tube inserts located at the top end of heat exchange tubes. The tube inserts have internal circumferential ribs. The ribs distribute a process flow into a uniform, annual film within the tube inserts and the tubes, and eliminate dry spots, even at low operating rates. This provides greater operating latitude, can improve operating efficiency and can reduce fouling.

11 Claims, 6 Drawing Sheets

(56) References Cited

U.S. PATENT DOCUMENTS

| | | | |
|---|---|---|---|
| 4,298,041 A | 11/1981 | Lagana | |
| 4,572,287 A | 2/1986 | Allo | |
| 8,221,708 B2 | 7/2012 | Seebauer | |
| 9,101,852 B2 | 8/2015 | Zaitsev | |
| 2005/0042042 A1 | 2/2005 | Clarke | |
| 2019/0366228 A1 * | 12/2019 | Olausson | B01D 1/30 |
| 2020/0030712 A1 | 1/2020 | Drumm | |

FOREIGN PATENT DOCUMENTS

| | | |
|---|---|---|
| SU | 1428398 A1 | 10/1988 |
| WO | 2006076923 A1 | 7/2006 |

* cited by examiner

FIGURE 3
FIGURE 4
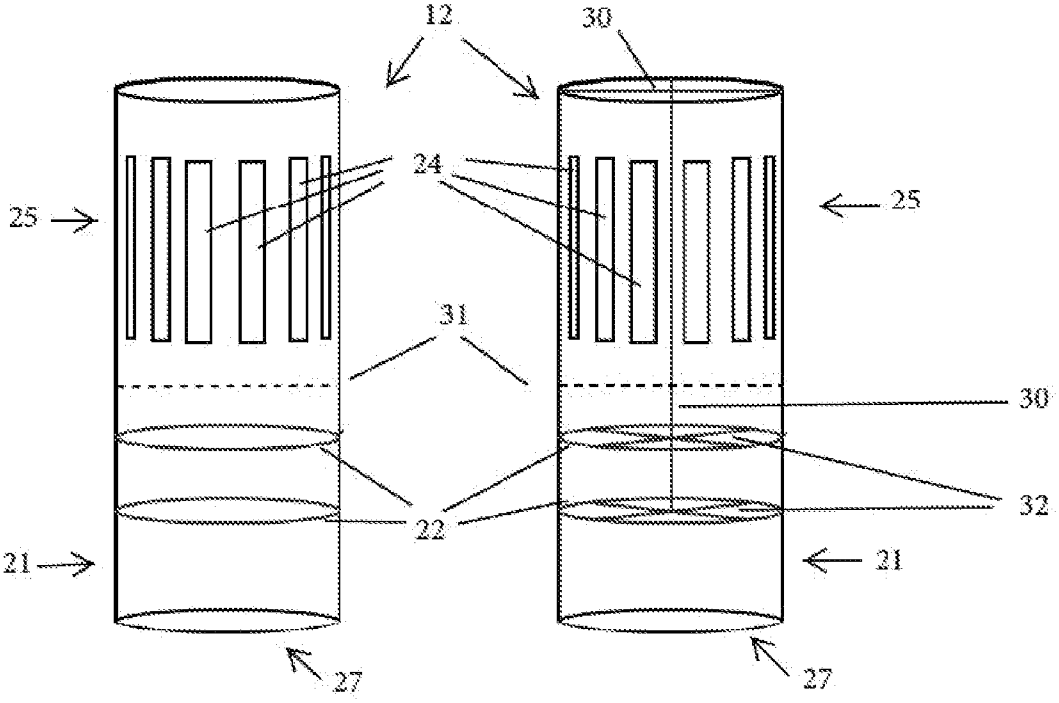
FIGURE 5
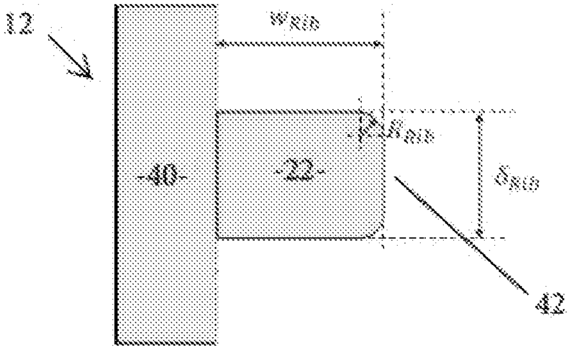
FIGURE 6
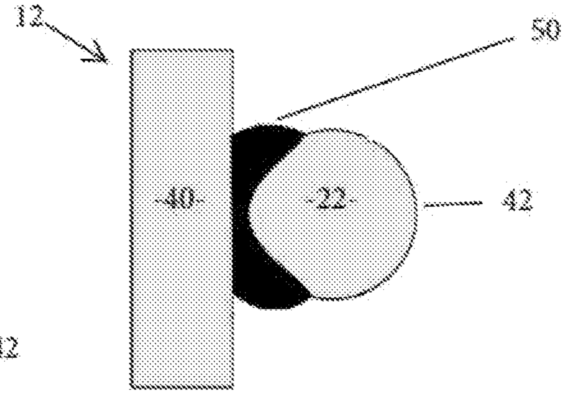

FALLING FILM APPARATUS AND METHOD FOR USING

The present invention relates to falling film apparatus, tube inserts for falling film apparatus, and methods for using a falling film apparatus, including separating a crude mixture of isocyanates in a falling film evaporator.

Falling film apparatus are in widespread industrial use as heat exchangers. They are useful as evaporators, for performing separations, for performing crystallizations, as well as in other applications. Falling film apparatus have multiple vertical tubes supported at each end by a tube sheet. The tubes are contained in a shell, through which a heat exchange fluid is circulated into contact with the vertical tubes to provide or remove heat from the tubes. A liquid to be so treated is passed downwardly through the interior of the tubes, where the liquid is heated or cooled, as the case may be.

Optimal operation of a falling film apparatus depends on forming a film of the liquid on all interior surfaces of the tubes. The liquid should wet all internal surfaces of each tube and in addition wet those surfaces uniformly and continuously throughout the operation of the device. Non-uniform distribution of the liquid can cause various problems, including reduced operating efficiencies. Unwanted reactions and fouling are common problems caused by improper liquid distribution in falling film apparatus.

For any liquid, there exists a theoretical minimum flow rate per tube that is necessary to maintain a film on the interior tube surfaces. Practically, it is necessary to operate at several times this theoretical minimum flow rate per tube. This constrains the range of operating rates that can be employed. Using higher flow rates promotes uniform wetting, but creates thicker films and can result in less efficient operation. Fluid passing through the device often must be recirculated one or more times to achieve the desired result, thereby increasing operating costs. Residence times are also increased, which can be problematic when, for example, the liquid is sensitive to time-temperature effects. Design improvements which allow a falling film apparatus to operate at flow rates closer to the theoretical minimum flow rate would be desirable.

This invention is in one aspect a falling film apparatus comprising:

(a) an outer shell enclosing an interior volume, (b) upper and lower tube sheets partitioning the interior volume into separate upper, middle and lower chambers, (c) one or more vertically oriented hollow tubes having open top and bottom ends, the hollow tubes each defining a fluid path from the upper chamber to the lower chamber, (d) for each at least one vertically oriented hollow tube, an associated tube insert located at the top end of the associated hollow tube, the tube insert comprising a hollow member having (i) an upper section residing above the tube sheet, (ii) a lower section extending into the associated hollow tube, (iii) one or more process fluid openings in the upper section for admitting a process fluid into the tube insert, (iv) an open bottom end for transferring a thin film of the process fluid from an interior surface of the tube insert onto an interior surface of the associated hollow tube; and (v) one or more circumferential ribs residing on the interior surface of the tube insert below the one or more process fluid opening(s).

FIG. 3 is a front sectional view of a tube insert for use in the invention.

FIG. 4 is a front sectional view of a second embodiment of a tube insert for use in the invention.

FIG. 5 is an enlarged sectional view of a circumferential rib of a tube insert for use in the invention.

FIG. 6 is an enlarged sectional view of a second embodiment of a circumferential rib of a tube insert for use in the invention.

Figure 1:
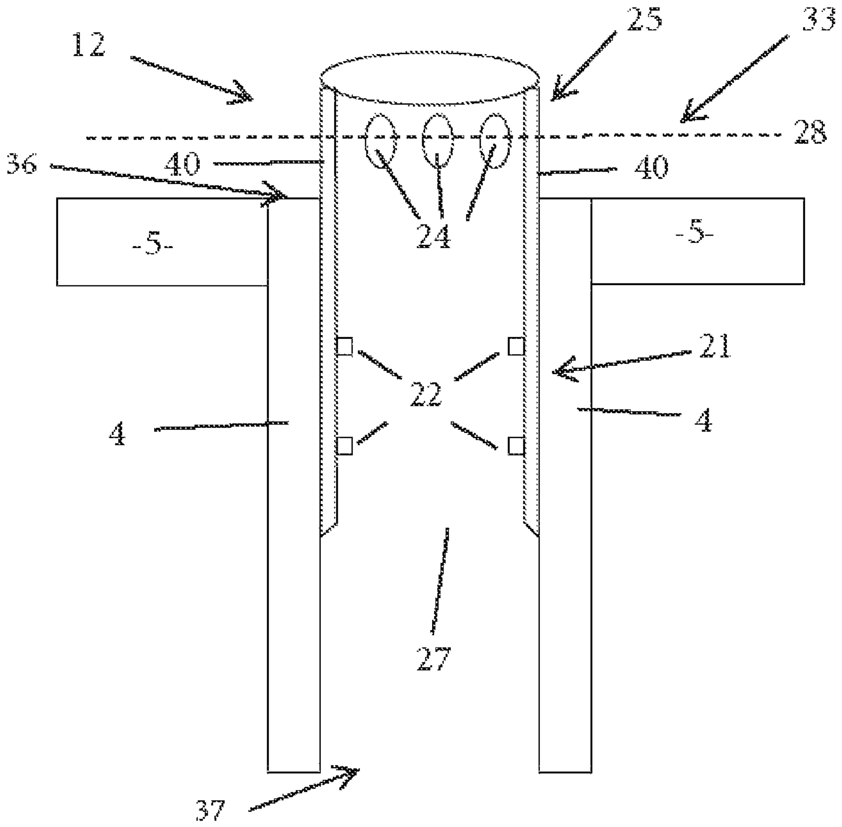
FIG. 1 is a front sectional view of an embodiment of an upper tube sheet, hollow tube and tube insert for use in a falling film apparatus of the invention.
Figure 2:
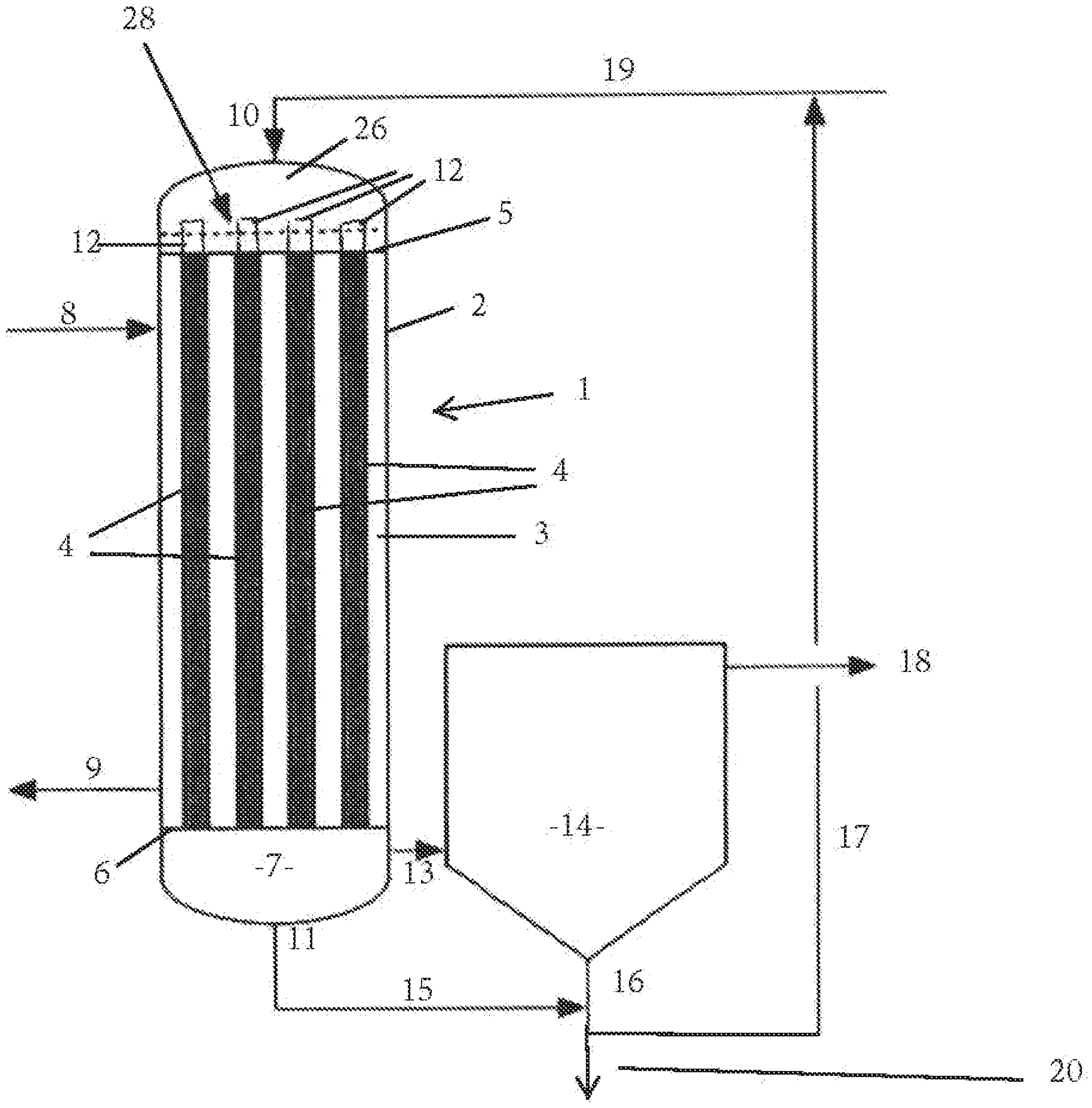
FIG. 2 is a schematic of a separation apparatus including a falling film evaporator of the invention.

Turning to FIG. 1, the invention includes tube sheet 5 and hollow tube 4. Hollow tube 4 has associated tube insert 12. In the cross-sectional view of a simplified apparatus shown in FIG. 1, only a single hollow tube 4 is present. More typically, multiple hollow tubes (and associated tube inserts 12) will be present. Each hollow tube 4 has open top end 36 and open bottom end 37. Each hollow tube 4 defines a fluid path from above to below tube sheet 5 through an opening in tube sheet 5 (and to below a lower tube sheet such as lower tube sheet 6 as shown in FIG. 2). An opening in tube sheet 5 accommodates each hollow tube 4. Tube sheet 5 is sealed around each hollow tube 4 such that a fluid flowing from above to below tube sheet 5 must pass through a hollow tube 4.

Hollow tubes 4 typically are cylindrical, with a circular cross-section, although hollow tubes 4 can assume other cross-sectional shapes if desired.

Hollow tubes 4 are vertically oriented, by which is it meant hollow tubes are oriented within 3 degrees of vertical, preferably within 1 degree of vertical.

Tube inserts 12 each are located at the top end of the associated hollow tube 4. As shown in FIG. 1, tube inserts 12 have an upper section 25 that resides above the upper surface of upper tube sheet 5 and a lower section 21 that extends into the associated hollow tube 4. Sidewall 40 defines an interior flow path through each tube insert 12.

Lower section 21 has outer cross-sectional dimensions equal to or smaller than the inside cross-sectional dimension of the associated hollow tube 4, so lower section 21 can extend into associated hollow tube 4. Lower section 21 may (as shown in FIG. 1) or may not extend below the level of tube sheet 5. In FIGS. 3, 4 and 7-10, dotted lines 31 indicate various possible locations of tube sheet 5 when tube inserts 12 are in place in the falling film apparatus.

Tube inserts 12 each have one or more process fluid openings 24 in upper section 25 for admitting a process fluid into the tube insert. "Process fluid" means any fluid or mixture of fluids (which may further contain a dispersed solid phase) that is passed through tube inserts 12 and hollow tubes 4, including a starting feed fluid introduced into tube inserts 12 and hollow tubes 4 as well as evaporated materials, reaction product or other products produced within hollow tubes. The process fluid contains at least one component that is liquid under the conditions that exist at the locations of circumferential ribs 22 of each tube insert 12. The composition of the process fluid may change as it travels through tube insert 12 and/or hollow tube 4.

In one embodiment, the process fluid opening is simply the open upper end of tube insert 12. In other embodiments, multiple process fluid openings 24 are provided in the wall of upper section 25 of tube insert 12, as shown in each of FIGS. 1, 3, 4, 7-10, 12 and 13. The size and shape of the process fluid openings may vary. Elliptical process fluid openings are shown in FIG. 1, being arranged about the circumference of upper section 25 of tube insert 12, and displaced longitudinally from the top edge of tube insert 12. In the embodiments shown in FIGS. 3, 4, 7 and 8, process fluid openings 24 are rectangular slots oriented longitudinally about the circumference of upper section 25 of tube insert 12, and are displaced longitudinally from the top edge of tube insert 12. In the embodiments shown in FIGS. 9 and 10, process fluid openings 24 take the form of triangular (FIG. 9) or rectangular (FIG. 10) notches arranged about the circumference of the top edge of tube insert 12.

Figure 12:
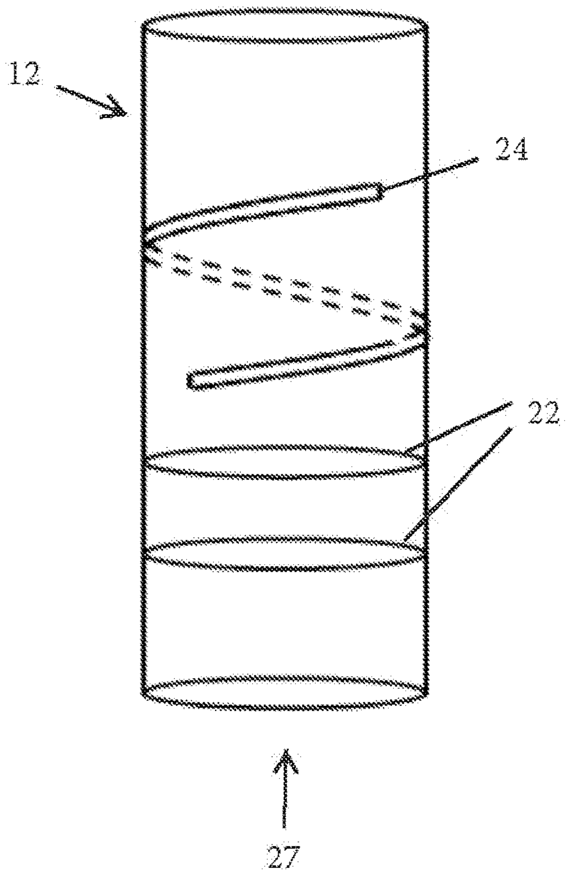
FIG. 12 is a front sectional view of a seventh embodiment of a tube insert for use in the invention.

In the embodiment shown in FIG. 12, process fluid opening 24 takes the form of helical slots that, as shown, are displaced longitudinally from the top edge of tube insert 12. Although only a single process fluid opening 24 is shown in FIG. 12, multiple helical slots preferably are present and are arranged about the circumference of the top edge of tube insert 12 so as to provide overlap between fluid streams entering tube insert 12 from the multiple helical slots. Fluid feed openings 24 can have other shapes as may be convenient or beneficial, such as squares, circles, rhombuses, ellipses, semi-circles, trapezoids, other polygons, or other arbitrary shape. The number of process fluid openings 24 provided in the wall of upper section 25 is not critical to the invention and may vary widely, such as from 2 to 20 or more. Similarly, the size of the multiple process fluid openings may vary considerably as may be necessary or desirable, and the multiple process fluid openings may or may not all be the same size.

Tube inserts 12 also each have an open bottom end 27 (FIGS. 1, 3, 4, 7-10, 12 and 13) in lower section 21 for discharging process fluids from each tube insert 12 into the associated hollow tube 4. Tube inserts 12 may be chamfered at open bottom end 27, as shown in FIG. 1, to produce a smooth transition from tube insert 12 into hollow tube 4.

Figure 7:
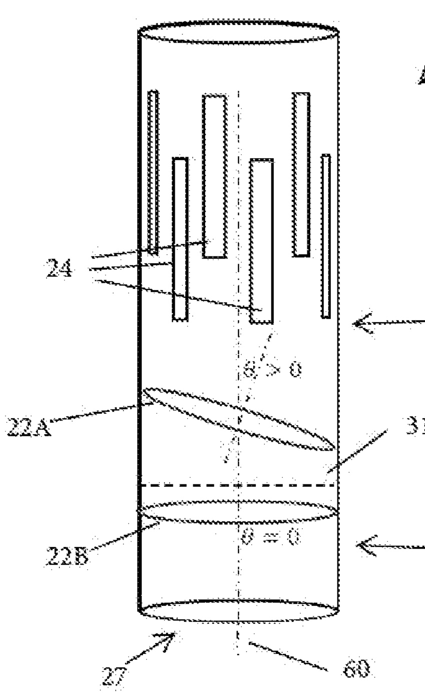
FIG. 7 is a front sectional view of a third embodiment of a tube insert for use in the invention.
Figure 8:
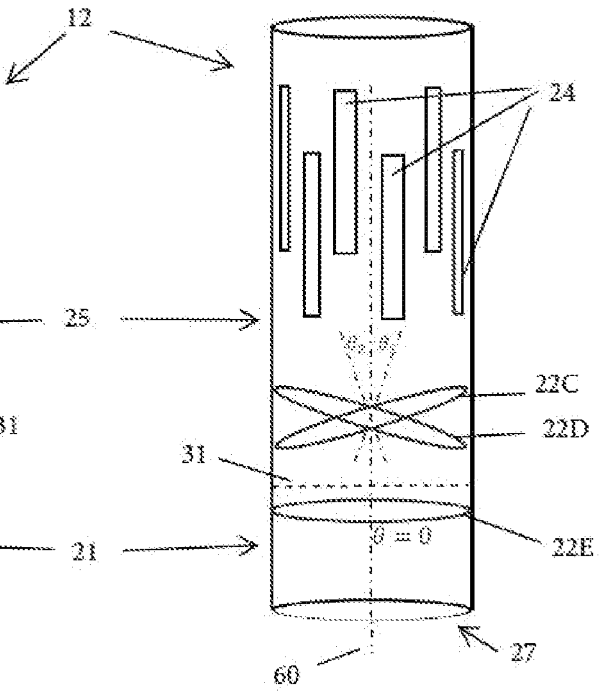
FIG. 8 is a front sectional view of a fourth embodiment of a tube insert for use in the invention.
Figure 9:
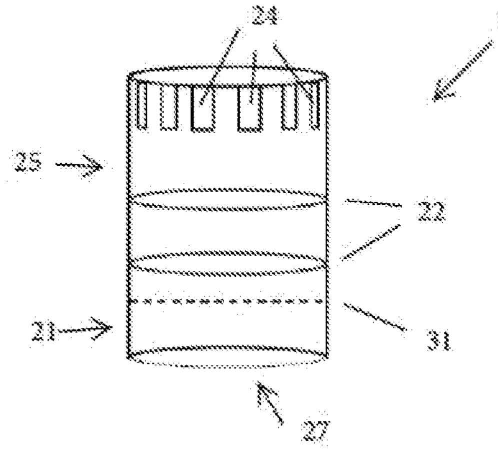
FIG. 9 is a front sectional view of a fifth embodiment of a tube insert for use in the invention.
Figure 10:
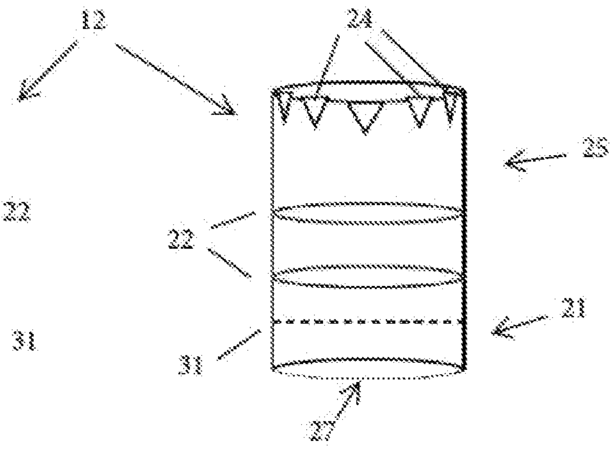
FIG. 10 is a front sectional view of a sixth embodiment of a tube insert for use in the invention.

Tube inserts 12 have one or more circumferential ribs 22 residing on the interior surface of tube inserts 12, below the process fluid opening(s). Circumferential ribs 22 may reside in upper section 25 of tube insert 12 (as is the case in FIGS. 9 and 10 and for circumferential ribs 22A, 22C and 22D in FIGS. 7 and 8, respectively), in lower section 21 (as is the case in FIGS. 1, 3, 4, and for circumferential ribs 22B and 22E in FIGS. 7 and 8, respectively) and/or at the boundary between upper section 25 and lower section 21 (i.e., a the level of upper tube sheet 5). As shown in FIGS. 7 and 8, circumferential ribs may reside in both upper section 25 and lower section 21.

Any arbitrary number of circumferential ribs may be provided. For example, the number of circumferential ribs is up to 10, up to 5 or up to 3, and only a single circumferential rib may be present.

By "circumferential", it is meant that the rib extends entirely around the interior wall of tube insert 12, forming a circle (if oriented perpendicular to longitudinal central axis 60 of tube insert 12, as shown in FIGS. 3, 4, 9, 10, 12 and 13) or an ellipse (if oriented non-perpendicularly to longitudinal central axis 60 of tube insert 12, as illustrated by circumferential ribs 22A, 22C and 22D in FIGS. 7 and 8. As shown in FIGS. 7 and 8, multiple circumferential ribs may be oriented at different angles to longitudinal central axis 60 if desired. In FIGS. 7 and 8, circumferential ribs 22A, 22C and 22D are oriented non-perpendicularly to longitudinal central axis 60 whereas circumferential ribs 22B and 22E are oriented perpendicularly to longitudinal central axis 60. All circumferential ribs 22 may be oriented at the same angle to longitudinal central axis 60.

Each circumferential rib 22 projects radially inward (i.e., toward the central longitudinal axis) from the interior surface of tube insert 12. The radial width $W_{Rib}$ (see FIG. 5) of each circumferential rib in some embodiments is at least 0.25 mm, and in some embodiments is at least 1 mm or at least 2.5 mm. The radial width $W_{Rib}$ may be, for example, as great as one-eighth the inner diameter $ID_{TI}$ of tube insert 12 ($ID_{TI}/8$), and in particular embodiments may be up to $ID_{TI}/12$ or $ID_{TI}/16$.

Each circumferential rib 22 has a longitudinal width $\delta_{Rib}$ (FIG. 5). $\delta_{Rib}$ in some embodiments is at least 0.25 mm, and in some embodiments is at least 1 mm or at least 2.5 mm. $\delta_{Rib}$ may be, for example, up to 25 mm, up to 10 mm, up to 7.5 mm or up to 5 mm.

The inward edges 42 of circumferential ribs 22 may be curved, and when curved the inward edges 42 may have a radius of curvature $R_{Rib}$ such that $R_{Rib} \leq \delta Rib/2$. When $R_{Rib} = \delta_{Rib}/2$ the inward edge 42 will have a semi-circular cross-section. $R_{Rib}$ may be $\leq \delta_{Rib}/4$, $\leq \delta_{Rib}/8$, or $\leq \beta_{Rib}/12$ and in some embodiments $R_{Rib} \geq \delta_{Rib}/32$, preferably $> \delta_{Rib}/24$ or $> \delta_{Rib}/16$.

Circumferential ribs 22 may be integral with sidewall 40 of tube insert 12, or may be a separately-produced member that is affixed into position within tube insert 12. If separately-produced, circumferential ribs 22 may be affixed to sidewall 40 by, for example, welding or gluing, such as weld or adhesive 50 (FIG. 6), or mechanically through the use of various fasteners, and hangers such as hanger apparatus 30 and supports 32 (FIG. 4). Circumferential slots for receiving circumferential ribs 22 may be provided in sidewall 40.

Figure 11:
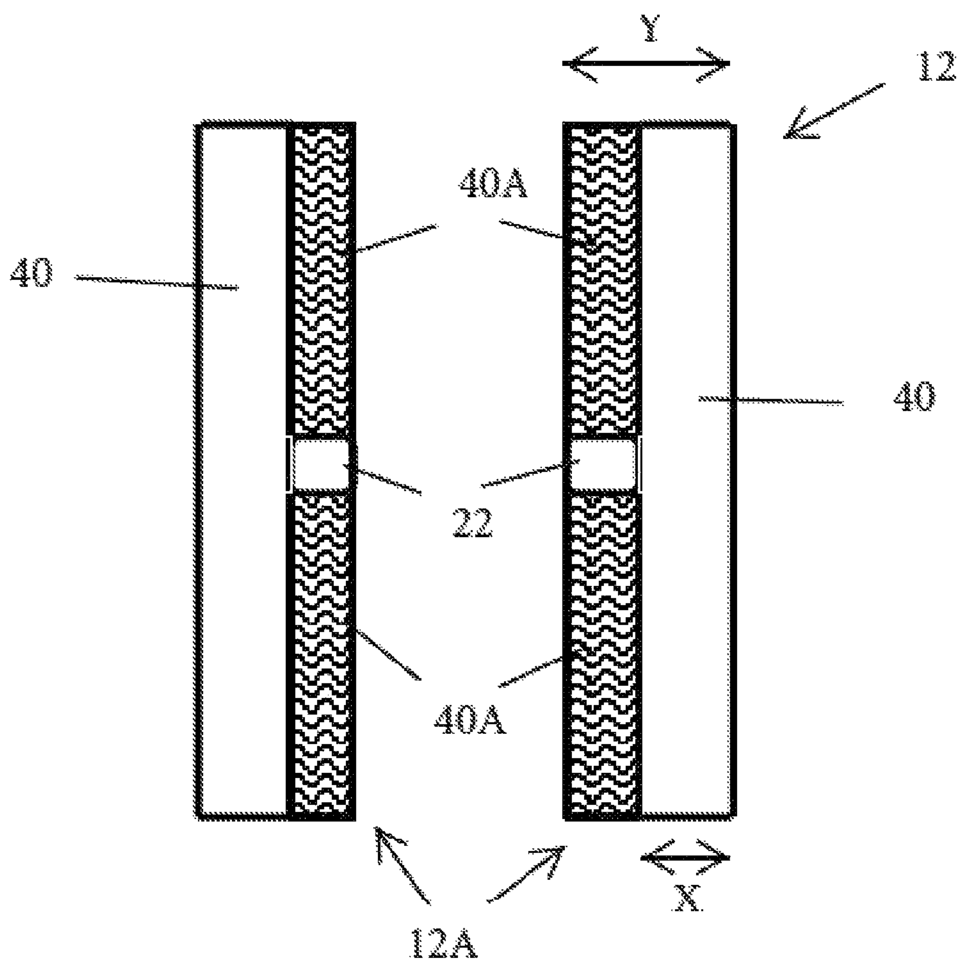
FIG. 11 is a front sectional view of a precursor for machining into a tube insert for use in the invention.

Integral circumferential ribs 22 may be produced by machining the interior of sidewall 40 of precursor tube 12A to remove wall material above and below the location of each circumferential rib 22, as shown in FIG. 11. Tube insert 12 is fabricated from a precursor tube 12A, which has a wall thickness Y greater than sidewall thickness X of tube insert 12 made therefrom. Shaded portions 40A of sidewall 40 in FIG. 11 are removed by machining to produce tube insert 12 having a sidewall thickness X and circumferential rib 22. The combined thickness of the wall and rib may be equal to original wall thickness Y.

Figure 13:
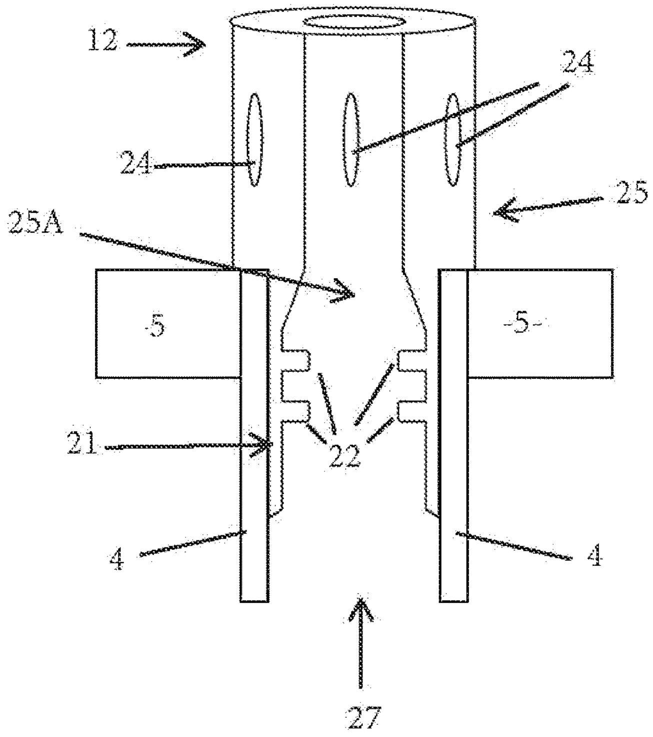
FIG. 13 is a front sectional view of an eighth embodiment of a tube insert for use in the invention.

The interior surface of sidewall 40 may be of uniform interior diameter (except for the ribs). In embodiments such as shown in FIG. 13, the interior surface of sidewall 40 in upper section 25 of tube insert 12 tapers outwardly in a region 25A starting below fluid process openings 24 to above ribs 22, thereby increasing the interior diameter of tube insert 12 through that region 25A of upper section 25. Such a design further facilitates smooth annular flow of the process fluids towards circumferential ribs 22.

In operation, a process fluid is introduced onto the upper surface of tube sheet 5 and upon reaching a certain height (such as indicated by liquid interface 28 in FIGS. 1 and 2) spills over into upper section 25 of tube inserts 12 through process fluid openings 24. Upon entering tube inserts 12, the process fluids are driven downward within the associated tube inserts 12 past circumferential ribs 22 by gravitational and/or differential pressure forces, continuing downward through lower section 21 of tube inserts 12, then out of tube inserts 12 through open bottom ends 27 and into hollow tubes 4. Circumferential ribs 22 capture the momentum of the falling process fluid to distribute the fluid evenly about the circumference of tube insert 12, forming a uniform film without dry spots. The uniform film is maintained as the process fluid passes through open bottom ends 27 and into and through associated hollow tubes 4.

Tube inserts 12 may further include one or more features such as flow deflectors that produce a tangential flow of process fluid entering the tube insert. The process fluid openings may be machined to produce a tangential flow of process fluid entering the tube insert.

Turning to FIG. 2, falling film apparatus 1 includes outer shell 2, which defines a vessel having an enclosed interior volume. Upper tube sheet 5 and lower tube sheet 6 partition the enclosed interior volume into upper portion 26 residing above upper tube sheet 5, middle portion 3 residing between upper tube sheet 5 and lower tube sheet 6, and lower portion 7 residing below lower tube sheet 6. Hollow tubes 4 define fluid paths from upper portion 26 through middle portion 3 to lower portion 7 of the enclosed interior volume. An opening in upper tube sheet 5 and an opening in lower tube sheet 6 accommodates each hollow tube 4. Upper tube sheet 5 and lower tube sheet 6 each are sealed around each hollow tube 4 such that a fluid flowing from upper portion 26 to below lower portion 7 must pass through a hollow tube 4.

Falling film heat apparatus 1 further includes at least one process fluid inlet port 10 for introducing a process fluid into upper portion 26 of the interior space enclosed by shell 2. Multiple process fluid inlet ports 10 may be provided. Falling film apparatus 1 further includes at least one process fluid outlet port 11 for removing process fluid(s) from lower portion 7 of the interior space enclosed by shell 2. Multiple process fluid outlet ports 11 may be provided. In the embodiment shown in FIG. 1, a separate gas outlet port 13 is provided for removing vapor from lower portion 7 of the space enclosed by shell 2.

Falling film apparatus 1 further includes at least one heat exchange fluid inlet port 8 for introducing a heat exchange fluid into interior space 3 and at least one heat exchange fluid outlet port 9 for removing heat exchange fluid from interior space 3.

In addition to the foregoing features, falling film apparatus 1 may include various optional components. A distributor may be provided to distribute process fluid onto upper tube sheet 5. A wide variety of distribution systems are available to ensure the uniformity of the liquid level on the top tube sheet. One type of distributor is a flat-bottomed container installed above upper tube sheet 5. The container has holes that allow the process fluid to flow onto upper tube sheet 5 between tube inserts 12. A spray distribution system sprays droplets of process fluid over upper tube sheet 5 and/or a flat-bottomed container installed above upper tube sheet 5. Other useful distributors include, for example, any of those described in U.S. Pat. Nos. 4,154,642, 4,199,537 and 9,101,852, and US Published Patent Application No. 2020/0030712. Other optional components include various valves, pumps, automated process control devices, and the like.

In operation, a process fluid is introduced into upper portion 26 via one or more inlet ports 10. The process fluid pools on the upper surface of upper tube sheet 5 and upon reaching a certain height (reference numeral 28 in FIGS. 1 and 2) spills over into upper section 25 of tube inserts 12 through process fluid openings 24. Upon entering tube inserts 12, the process fluid falls under force of gravity and/or applied pressure downwardly past circumferential ribs 22, through lower section 21 of tube inserts 12, then out of tube inserts 12 through open bottom ends 27 and into and through hollow tubes 4, ultimately passing into lower portion 7 of heat exchange apparatus 1. As described before, the falling process fluid upon passing circumferential ribs 22 becomes distributed evenly about the circumference of tube insert 12, forming a uniform film without dry spots. The uniform film is maintained as the process fluid passes through open bottom ends 27 and into and through associated hollow tubes 4.

In heat exchange operations, hollow tubes 4 are maintained at a different temperature than the process fluid introduced via feed inlet port(s) 10, and thus heat is exchanged between hollow tubes 4 and the process fluid. The hollow tube temperature may be higher or lower than that of the incoming process fluid. The hollow tube temperature typically is higher for operations such as evaporations, pasteurizations and performing chemical reactions, and lower for operations such as crystallizations.

Heat is supplied or removed from hollow tubes 4 via a heat exchange fluid that is introduced into middle portion 3 via heat exchange fluid inlet port 8. The heat exchange fluid circulates within interior space 3, between upper tube sheet 5 and lower tube sheet 6 and in contact with hollow tubes 4, heating or cooling hollow tubes 4 (as the case may be), and is withdrawn through heat exchange fluid outlet port 9. The heat exchange fluid may be a liquid and/or a gas. Some or all of the heat exchange fluid may undergo a phase change within the vessel; steam, for example, may partially or entirely condense within the vessel. Heat exchange fluids are selected at least partially with the desired operating temperatures in mind. Examples of other heat exchange fluids include liquid water, air, nitrogen, argon, helium, liquid and/or gaseous halocarbons (including hydrohalocarbons), silicone fluids, ethylene glycol, propylene glycol and other alkylene glycols and polyalkylene glycols, various alkylated aromatic compounds, various polyester compounds, and the like.

In some embodiments, the falling film apparatus of the invention is used to perform evaporations. In such embodiments, the process fluid is a single-component liquid, which is to be evaporated within hollow tubes 4 or, more typically, a multi-component fluid containing at least one component that is to be separated from at least one other component by fractional distillation within hollow tubes 4. Evaporations typically produce one or more gaseous products representing component(s) of the process fluid that become evaporated within hollow tubes 4, and one or more liquid products which are components of the process fluid that pass through hollow tubes 4 without evaporating. It is generally preferred to establish a flow of gases downward through hollow tubes 4 so that gaseous products are removed from the bottom of hollow tubes 4; however it is within the scope of the invention to remove gaseous products from the top of hollow tubes 4.

The falling film apparatus shown in FIG. 2 is particularly adapted for performing evaporations. The annular film of process fluid flowing downwardly into and through hollow tubes 4 is heated in hollow tubes 4, and at least a portion of one or more components of the process is volatilized to form a gas.

In the embodiment shown in FIG. 2, both the volatilized (gaseous) and non-volatilized components of the process fluid flow into lower portion 7 of the vessel, where they are separated. In the embodiment shown, volatilized component(s) are removed from lower portion 7 via line 13, through which they are transferred to optional gas-liquid separator 14 to remove entrained non-volatilized material from the gaseous products. The gaseous products are then recovered via line 18.

Non-volatilized component(s) of the process fluid are removed from lower portion 7 of the vessel via outlet port 11 and line 15. In the optional arrangement shown, non-volatilized component(s) removed via line 15 are combined with additional quantities of non-volatilized component(s) removed from gas-liquid separator 14 via line 16. A non-volatilized product stream is withdrawn via recovery line 20.

All or a portion of the non-volatilized components recovered from falling film apparatus 1 may be recycled back into falling film apparatus 1 if desired, as is the case, for example, of incomplete evaporation of volatile components of the process fluid. In FIG. 1, for example, a recycle stream is taken via line 17, recombined with fresh process fluid, and the mixture fed into upper portion 26 of enclosed interior space 3 via line 19 and inlet port 10.

An important advantage of this invention is that annular films of liquid components of the process fluid can be formed without dry spots on all internal surfaces of tube inserts 12 and hollow tubes 4, even at low liquid flow rates. Lower liquid flow rates produce thinner films. Thinner films allow for faster and more uniform heating or cooling of the process fluid and, in the case of evaporations, more complete removal of volatile components from the process fluid. As a result, less material needs to be recycled. Recycled material experiences a more severe thermal history than material processed in a single pass, as the recycled material is exposed to the elevated temperatures for a much longer time period. When the recycled material contains heat-sensitive components, the ability to reduce recycling, thereby reducing exposure times to elevated temperatures, is often a significant advantage.

The ability to produce annular films without dry spots at low flow rates also extends the range of conditions at which the falling film apparatus can be operated. For example, it may be desirable or necessary to operate at relatively low flow rates at certain times, such as during start-ups or shutdowns, without fouling the apparatus or producing non-prime material. The falling film apparatus of the invention permits operation over a wide range of flow rates.

Flow rates though a hollow tube apparatus can be expressed in terms of a minimum wetting rate $\Gamma_{min}$, which is a function of the contact angle θ (between the entering process fluid and the tube or insert), and the surface tension σ, viscosity μ, gravitational constant g and density ρ of the process fluid, as follows:

$$\Gamma_{min} = 1.69\left(\frac{\mu\rho}{g}\right)^{1/5}(\sigma(1-\cos\theta))^{3/5} \qquad \text{(Equation 1)}$$

Previous falling film apparatus with tube inserts typically operate at a flow rate of 5 or more times $\Gamma_{min}$; they do not produce uniform annular films at lower flow rates. By contrast, the falling film apparatus of this invention operates well at flow rates as low as 1.5 $\Gamma_{min}$ or even lower, and also operate well at much greater flow rates. Thus, in some embodiment of the invention, the falling film apparatus of the invention is operated at a flow rate of 1.5 $\Gamma_{min}$ to 10 $\Gamma_{min}$, 1.5 $\Gamma_{min}$ to 5.0 $\Gamma_{min}$ or 1.5 to 3 $\Gamma_{min}$.

The falling film apparatus of the invention is useful for performing many types of separations, including producing concentrated foods such as concentrated fruit juices and evaporated and/or condensed milk, manufacturing alcoholic beverages such as whiskeys, as well as in many chemical and/or petrochemical processes.

Among the many chemical separations for which the falling film apparatus is useful is the separation of a crude isocyanate mixture produced by phosgenating a mixture of methylene dianiline with higher polymethylene polyanilines. In such a separation, diphenyl methylene diisocyanate (MDI) is separated from higher polymethylene polyphenylene polyisocyanates (having three or more phenyl isocyanate groups) by passing the crude mixture through the falling film apparatus operated at a tube temperature sufficient to volatilize the MDI but not the higher polymethylene polyphenylene polyisocyanates. This produces an MDI-rich vapor stream that may contain, for example, at least 98% by weight MDI, and a liquid stream of polymethylene polyphenylene polyisocyanates that is, relative to the starting crude mixture, enriched in polymethylene polyphenylene polyisocyanate and depleted in MDI.

Comparative Sample A

A hollow stainless steel tube having an inner diameter of 4.47 cm is fitted in a tube sheet positioned in the bottom surface of a container. A tube insert having an outer diameter of 4.47 cm and wall thickness of 0.018 cm is inserted into the hollow tube such that an upper section resides above the level of the tube sheet and a lower section resides within the hollow tube below the level of the tube sheet. Eight process fluid openings in the form of longitudinal slots 3 cm in width are spaced evenly about the circumference of the upper section of the tube insert. Associated with each of the process fluid openings is a flow deflector positioned at an angle of about 20 degrees to the open face of the slot. The flow deflectors produce a tangential flow entry of the process fluid into the tube insert. The interior surface of the tube insert below the process fluid openings is smooth and of a constant diameter.

A fluid having (at the temperature of the experiment) a density of 1106 $kg/m^3$, a viscosity of 1.9 cP, a surface tension of 31 mN/m and an advancing contact angle with stainless steel of 60 degrees is poured into the container to create a flow rate of 82 kg/h, yielding a wetting rate Γ of 0.162 kg/m-s. The minimum wetting rate $\Gamma_{min}$ for this fluid is 0.099 kg/m-s, as calculated according to Equation 1 above. The operating ratio $\Gamma/\Gamma_{min}$ is 1.64. Under these conditions, the liquid forms rivulets on the inner walls of the tube insert and does not uniformly wet the walls. A uniform annular film is produced only when the flow rate is increased to produce an operating ratio $\Gamma/\Gamma_{min}$ of greater than 4.

Example 1

Comparative Sample A is repeated, except this time the tube insert has 2 circumferential ribs in the inner wall beneath the process fluid openings. $R_{Rib}$ is 0.762 mm, $W_{Rib}$ is 2.03 mm, and $\delta_{Rib}$ is 1.52 mm. A uniform film forms as the process fluid passes downwardly past the circumferential ribs, wetting all interior surfaces of the tube insert, at the operating ratio $\Gamma/\Gamma_{min}$=1.64.

Example 2

Comparative Sample A is again repeated, except this time the tube insert lacks the flow deflectors and there are three circumferential ribs. The circumferential ribs have the same dimensions as those described in Example 1. At the operating ratio $\Gamma/\Gamma_{min}$=1.64, a uniform film forms as the process fluid passes downwardly past the 33 circumferential ribs, even without the benefit of tangential fluid entry. All interior surfaces of the tube insert become wetted.

What is claimed is:

1. A falling film apparatus comprising:

(a) an outer shell enclosing an interior volume;

(b) upper and lower tube sheets partitioning the interior volume into separate upper, middle and lower chambers;

(c) one or more vertically oriented hollow tubes having open top and bottom ends, each vertically oriented hollow tube defining a fluid path from the upper chamber to the lower chamber;

and for each vertically oriented hollow tube;

(d) an associated tube insert located at the top end of the vertically oriented hollow tube, the associated tube insert comprising a hollow member having;

(i) an upper section residing above the upper tube sheet, (ii) a lower section extending into the vertically oriented hollow tube, (iii) one or more process fluid openings in the upper section for admitting a process fluid into the associated tube insert, (iv) an open bottom end for transferring a thin film of the process fluid from an interior surface of the associated tube insert onto an interior surface of the vertically oriented hollow tube, and (v) one or more circumferential ribs residing on the interior surface of the associated tube insert below the process fluid opening(s);

wherein the vertically oriented hollow tube(s) and associated tube insert(s) each have circular cross-sections, each circumferential rib has a radial width $W_{Rib}$ of at least 0.25 mm and at most $ID_I/8$, wherein $ID_I$ represents an inner diameter of the associated tube insert, and each circumferential rib has curved inward edges having a radius of curvature $R_{Rib}<\delta_{Rib}/2$, wherein $\delta_{Rib}$ represents the longitudinal thickness of the circumferential rib.

2. The falling film apparatus of claim 1, wherein the upper section of the associated tube insert is adapted to produce a tangential flow of process fluid into the associated tube insert.

3. The falling film apparatus of claim 1, wherein the one or more process fluid openings in the upper section of the associated tube insert are helical slots.

4. The falling film apparatus of claim 1, further comprising:

(e) at least one process fluid inlet port for introducing a process liquid into the upper chamber and into contact with an upper surface of the upper tube sheet;

(f) at least one process fluid outlet port for removing treated process fluid from the lower chamber;

(g) at least one heat exchange fluid inlet port for introducing a heat exchange fluid into the middle chamber; and (h) at least one heat exchange fluid outlet port for removing the heat exchange fluid from the middle chamber.

5. The falling film apparatus of claim 1, further comprising a process fluid distributor above the upper tube sheet.

6. The falling film apparatus of claim 1, further comprising:

(e) at least one process fluid inlet port for introducing a process liquid into the upper chamber and into contact with an upper surface of the upper tube sheet.

7. The falling film apparatus of claim 1, further comprising:

(f) at least one process fluid outlet port for removing at least-treated process fluid from the lower chamber.

8. The falling film apparatus of claim 1, further comprising:

(g) at least one heat exchange fluid inlet port for introducing a heat exchange fluid into the middle chamber.

9. The falling film apparatus of claim 1, further comprising:

(h) at least one heat exchange fluid outlet port for removing heat exchange fluid from the middle chamber.

10. A process for separating components of a liquid mixture, the process comprising:

introducing a process fluid containing the liquid mixture into the falling film apparatus of claim 1;

flowing the process fluid through the associated tube insert(s) of the falling film apparatus to form an annular film of the process fluid; and then transferring the film of the process fluid into heated hollow tube(s) of the falling film apparatus and flowing the film downwardly through the heated hollow tube(s), whereby at least one component of the liquid mixture is at least partially vaporized from the film as the film flows downwardly through the heated hollow tube(s), and at least one component of the liquid mixture is not volatilized.

11. The process of claim 10, wherein the process fluid contains diphenylmethane diisocyanate and polymethylene polyphenylene polyisocyanates;

whereby diphenylmethane diisocyanate is at least partially vaporized from the film as the film flows downwardly through the heated hollow tube(s) to produce a vapor stream containing diphenylmethane diisocyanate and a liquid stream that is, relative to the process fluid, enriched in polymethylene polyphenylene polyisocyanates and depleted in diphenylmethane diisocyanate.

* * * * *